United States Patent [19]

Cosgrove et al.

[11] 4,166,118

[45] Aug. 28, 1979

[54] USE OF CHLORHYDROXYQUINOLINE TO INHIBIT GROWTH OF MYCOPLASMAS

[75] Inventors: Raymond F. Cosgrove, Wallasey; Sandra Baines, Thingwall, both of England

[73] Assignee: E. R. Squibb & Sons, Inc., Princeton, N.J.

[21] Appl. No.: 947,318

[22] Filed: Oct. 2, 1978

[30] Foreign Application Priority Data

Oct. 13, 1977 [GB] United Kingdom ............... 42721/77

[51] Int. Cl.² ............................................. A61K 31/47
[52] U.S. Cl. ................................................... 424/258
[58] Field of Search .......................................... 424/258

[56] References Cited

PUBLICATIONS

Chem. Abst. Chem. Substance Index–9th Coll, vol. 76–85, (1972–1976), p. 34851cs.
Goot et al.–Chem. Abst., vol. 84, (1976), p. 145358s.
Merck Index–9th Edit., (1976), p. 2143.

*Primary Examiner*—Sam Rosen
*Attorney, Agent, or Firm*—Lawrence S. Levinson; Burton Rodney

[57] ABSTRACT

A method is provided for inhibiting growth of mycoplasmas by treatment with chlorhydroxyquinoline. Compositions containing chlorhydroxyquinoline for use in the above method are also provided.

7 Claims, No Drawings

USE OF CHLORHYDROXYQUINOLINE TO INHIBIT GROWTH OF MYCOPLASMAS

The present invention relates to a method for inhibiting and preventing growth of mycoplasmas employing chlorhydroxyquinoline and to compositions for use in such method.

Chlorhydroxyquinoline is known as having activity against bacteria (which have cell walls), fungi and protozoa. In particular, it has been found to be useful in the treatment of acne.

It is well known that many bactericidal agents, such as penicillins, which are effective against bacteria may not be effective against mycoplasma. These bactericides function by destroying the cell wall of the bacteria. However, mycoplasmas, the smallest free-living microorganisms, lack a cell wall and are resistant to penicillin and other agents.

It has now been surprisingly found that chlorhydroxyquinoline is active against mycoplasmas and thus may be employed in the treatment of diseases caused by same. More particularly, it has been found that chlorhydroxyquinoline is active against *Mycoplasma hyorhinis* (known to be associated with upper respiratory tract disease in pigs), *Mycoplasma hyopneumoniae* (known to cause chronic pneumonia in swine), *Mycoplasma gallisepticum* (known to cause chronic respiratory disease in poultry), *Mycoplasma synoviae* (know to cause infectious synovitis and air sacculitis in chickens), *Mycoplasma meleagridis* (known to cause skeletal lesions of turkeys), *Mycoplasma agalactiae* (known to cause mastitis in cattle, sheep and goats), *Mycoplasma bovigenitalium* and *Mycoplasma bovirhinis* (known to cause mastitis in cattle), *Mycoplasma mycoides* var. capri (known to cause contagious pleuropneumonia in goats), *Mycoplasma mycoides* var. mycoides (known to cause contagious bovine pleuropneumonia) and Mycoplasma spp. (known to cause endometritis in cattle, sheep and goasts). Chlorhydroxyquinoline is also active against *Acholeplasma laidlawii* (G23/6, B), Iowa 695 cloned, Type 8FB Serotype, W.R.I. 431/10 Serotype.

According to the invention, in one of its aspects, a method is provided for inhibiting the growth of mycoplasma which comprises treating mycoplasma species with a growth inhibiting amount of chlorhydroxyquinoline.

The invention is intended for the treatment of animals, particularly non-human mammals, and it provides methods and compositions of chlorhydroxyquinoline which are specifically intended and suitable for this purpose.

When investigating the present invention, chlorhydroxyquinoline was found to have a minimum inhibitory concentration (MIC) with respect to a broad range of mycoplasmas, this MIC ranging from about 0.1 to about 4 $\mu$g/ml. Examples, including examples of specific minimum inhibitory concentrations of chlorhydroxyquinoline, vis-a-vis specific mycoplasma species, will be given hereinafter.

Thus, for example, endometritis associated with Mycoplasma spp. may be effectively treated by the administration of chlorhydroxyquinoline in the form of vaginal suppositories.

Mastitis associated with *Mycoplasma agalactiae*, *Mycoplasma bovirhinis* and *Mycoplasma bovigenitalium* may be effectively treated by infusion of chlorhydroxyquinoline into the udder through the teat canal.

In either of the above cases, the chlorhydroxyquinoline will be administered to provide an amount thereof within the range of from about 1 milligram per kilogram of animal body weight per day to about 100 milligrams per kilogram of animal body weight per day, and preferably from about 2.5 milligrams per kilogram of animal body weight per day to about 25 milligram per kilogram of animal body weight per day. The above dosages may be administered in a single dose or divided dosages of, for example, 2 to 4 times per day for one or more days, up to 14 days, until the infection is brought under control.

The unit dosage suppository composition is prepared by intimately and uniformly mixing the chlorhydroxyquinoline with suitable finely divided diluents, suspending agents, fillers, disintegrating agents and/or binders such as starch, lactose, talc, magnesium stearate, vegetable gums and the like and are compounded by techniques generally known in the art.

Chlorhydroxyquinoline which is to be administered by infusion is suspended in water or other physiologically acceptable diluent which is nonreactive with respect to the chlorhydroxyquinoline and may be administered with safety to the animals.

The following Examples demonstrate the effectiveness of chlorhydroxyquinoline in inhibiting growth of various mycoplasma species.

EXAMPLE 1

The mycoplasma species used are listed in Table 1. Organisms 1–8 are obtained from Liverpool University's Veterinary Field Station (Leahurst); organisms 9 and 10 from the National Collection of Type Cultures; and organisms 11 and 12 from the Royal Veterinary College, London. The organisms are grown and tested for their susceptibility to chlorhydroxyquinoline in modified Chanock Medium (20 ml inactivated horse serum; 10 ml yeast extract; 1 ml 10% glucose solution; 1 ml 1% nicotinamide adenine dinucleotide solution; 1 ml 10% arginine solution, 1 ml 5% thallous acetate solution; 100,000 units benzylpenicillin; 2 ml 0.1% phenol red; 1.47 g Difco PPLO broth; 70 ml distilled water).

Chlorhydroxyquinoline is dissolved in dimethylformamide (D.M.F.) at a concentration of 8000 $\mu$g/ml. Doubling dilutions are made in D.M.F. and 0.05 ml of each dilution added to 6 ml aliquots of sterile medium in bijou ($\frac{1}{4}$ oz) bottles. 0.5 ml of a 24 hour actively growing culture of mycoplasma is added to each bijou bottle. The final concentrations of chlorhydroxyquinoline in the medium ranged from 61.5 $\mu$g/ml to 0.12 $\mu$g/ml. Control cultures, with 0.5 ml D.M.F. are included with each M.I.C. determination. The cultures are incubated at 37° C. for 48 hours and the M.I.C. determined. 0.5 ml aliquots are then removed from the bottle containing the highest concentration of chlorhydroxyquinoline which still allow normal or nearly normal growth, and transferred to another series of bottles containing a range of chlorhydroxyquinoline concentrations similar to those above. Successive transfers are made every 48 hours until ten transfers are completed.

As shown in Table 1, M.I.C. figures are all around the 1 $\mu$g/ml level and there is no significant development of resistance over the test period of ten transfers.

The results of all the strains examined, whether pathogenic or saprophytic, fresh-field isolates or serotypes, give similar results, namely, that chlorhydroxyquinoline has significant antimycoplasmal activity.

TABLE 1

M.I.C. and Resistance Studies of
Chlorhydroxyquinoline Against Mycoplasma Species

| Organism | Initial M.I.C. (ug/ml) | M.I.C. After 5 Passages (ug/ml) | M.I.C. After 10 Passages (ug/ml) |
|---|---|---|---|
| 1. *Acholeplasma laidlawii* G23/6 | 0.96 | 1.92 | 1.92 |
| 2. *A. laidlawii* B | 0.96 | 0.96 | 0.96 |
| 3. Iowa 695 cloned | 1.92 | 1.92 | 3.85 |
| 4. *M. synoviae* (Freshfield isolate) | 0.96 | 0.96 | 0.96 |
| 5. Type 8 FB Serotype | 0.96 | 0.96 | 0.96 |
| 6. W.R.I. 431/10 Serotype | 0.96 | 0.96 | 1.92 |
| 7. *M. gallisepticum* Serotype A | 0.96 | 1.92 | 1.92 |
| 8. *M. gallisepticum* A. 514 | 0.96 | 1.92 | 1.92 |
| 9. *M. bovigenitalium* NCTC 10122 | 0.24 | 0.12 | 0.12 |
| 10. *M. agalactiae* var. bovis NCTC | 0.96 | 1.92 | 1.92 |
| 11. *M. hyopneumoniae* | 0.24 | 0.48 | 0.48 |
| 12. *M. hyorhinis* | 0.24 | 0.12 | 0.12 |

EXAMPLE 2

A typical chlorhydroxyquinoline suppository formulation suitable for administration against cattle infected with Mycoplasma spp. is set out below.

Chlorhydroxyquinoline—10 mg
Hydrogenated vegetable oils—2.7 g

The above suppository is prepared by mixing the hydrogenated vegetable oils in a stainless steel kettle at 50°–60° C. While stirring, micropulverized chlorhydroxyquinoline is added. The mixture is cooled almost to its congealing point and poured into suitable chilled suppository molds.

EXAMPLE 3

A typical chlorhydroxyquinoline infusion formulation suitable for administration against cattle infected with *Mycoplasma bovirhinis* is set out below.

Chlorhydroxyquinoline—10 mg
Aluminum monostearate—0.12 g
Butylated hydroxy anisole—1.2 g
Peanut oil—sufficient to make—6 ml The above formulation is prepared as follows. Butylated hydroxy anisole is dissolved in the peanut oil. The resulting mixture is filtered through a suitable sterile Millipore membrane filter under nitrogen pressure and transferred to a sterile stainless steel kettle. Aluminum monostearate is added and the mixture heated, with stirring, to 140° C. for about 1 hour. The mixture is cooled to 60°–70° C. with stirring and then cooled to room temperature with no stirring.

Micropulverized chlorhydroxyquinoline is added with stirring. The resulting suspension is then poured through a suitable sterile homogenizer or colloid mill and a formulation suitable for infusion collected.

What is claimed is:

1. A method of inhibiting the growth of mycoplasma which comprises treating mycoplasma species with a growth inhibiting amount of chlorhydroxyquinoline.

2. The method as defined in claim 1 wherein said mycoplasma species is *Acholeplasma laidlawii, M. synoviae, M. gallisepticum, M. bovigenitalium, M. bovirhinis, M. agalactiae, M. hyopneumoniae, M. hyorhinis, M. mycoides* var. capri, *M. mycoides* var. mycoides, *M. meleagridis,* Iowa 695 cloned, Type 8 FB Serotype or W.R.I. 431/10 Serotype.

3. The method as defined in claim 1 wherein the minimum inhibitory concentration of chlorhydroxyquinoline in $\mu$g/ml ranges from about 0.1 to about 4.

4. The method as defined in claim 1 wherein the chlorhydroxyquinoline is administered to an infected mammalian host in an amount within the range of from about 1 milligram per kilogram of body weight per day to about 100 milligrams per kilogram of body weight per day.

5. The method as defined in claim 4 wherein the chlorhydroxyquinoline is administered by infusion through the teat canal of cattle, sheep or goats to combat mastitis.

6. The method as defined in claim 4 wherein the chlorhydroxyquinoline is administered in suppository form to a non-human animal to combat endometritis.

7. A composition for use in inhibiting the growth of mycoplasma which comprises a mycoplasma growth inhibiting amount of chlorhydroxyquinoline and a pharmaceutically acceptable carrier comprising aluminum monostearate, butylated hydroxy anisole and peanut oil.

* * * * *